United States Patent [19]

Alperovich et al.

[11] Patent Number: 5,211,646

[45] Date of Patent: May 18, 1993

[54] CRYOGENIC SCALPEL

[76] Inventors: Boris I. Alperovich, ulitsa Dzerzhinskogo, 36, kv. 47; Ljutsia M. Paramonova; Alexandr I. Paramonov, both of ulitsa Ferentsa Mjunnikha, 3, kv. 25, all of, Tomsk, U.S.S.R.

[21] Appl. No.: 762,645

[22] Filed: Sep. 19, 1991

Related U.S. Application Data

[63] Continuation of Ser. No. 495,390, Mar. 16, 1990.

[51] Int. Cl.$^5$ .............................................. A61B 17/36
[52] U.S. Cl. ...................................... 606/23; 606/22; 606/169; 606/25
[58] Field of Search .................. 606/20–25, 606/167, 169, 171

[56] References Cited

U.S. PATENT DOCUMENTS

| | | | |
|---|---|---|---|
| 2,714,890 | 8/1955 | Vang | 606/169 |
| 2,845,072 | 7/1958 | Shafer | 606/169 |
| 3,832,776 | 9/1974 | Sawyer | 606/169 |
| 3,933,156 | 1/1976 | Riggi | 606/25 |
| 4,724,834 | 2/1988 | Alperovich et al. | 606/23 |
| 4,823,790 | 4/1989 | Alperovich et al. | 606/24 |
| 4,832,022 | 5/1989 | Tjulkov et al. | 606/22 |

FOREIGN PATENT DOCUMENTS 2628131 12/1977 Fed. Rep. of Germany ...... 606/169

Primary Examiner—Peter A. Aschenbrenner
Attorney, Agent, or Firm—Burgess, Ryan & Wayne

[57] ABSTRACT

A cryogenic scalpel comprises a hollow housing, a pressure source, a working portion connected to the hollow housing and having a heat-exchanger communicating with the pressure source through a piping, and a blade. The scalpel comprises also a source of electromechanical oscillations located in a hollow housing and establishing reciprocating motion of the working portion, and a unit for imparting electromechanical oscillations to the working portion, interconnected to the source of electromechanical oscillations.

10 Claims, 3 Drawing Sheets

CRYOGENIC SCALPEL

This application is a continuation of application Ser. No. 495,390, filed Mar. 16, 1990.

FIELD OF THE INVENTION

This invention relates generally to medical appliances and more specifically, to cryogenic scalpels.

The invention can find application in surgery for operative procedures on parenchymatous organs, including the liver, kidneys, spleen, pancreas, and lungs.

BACKGROUND OF THE INVENTION

One state-of-the-art cryogenic surgical instrument is known to comprise a body and a working portion, which consists of a heat-exchanger and a blade. The body includes inlet and outlet pipings for the refrigerant to pass, while the heat-exchanger has a blade heating coil, said blade being made of a Pt-Ir alloy.

Such an instrument, however, features a low refrigerating capacity of its heat-exchanger, while a low rate of biologic tissue dissection with such an instrument is due to a consecutive connection of cold and heat to the working portion, i.e., the heat-exchanger and the heating coil operate alternatively. Thus, a hemostatic effect attainable by said instrument is also inadequate (cf. a prospectus Lumberoupoulos, 1967, the Federal Republic of Germany).

One more prior-art cryogenic scalpel is known to comprise a hollow housing and a working portion connected thereto and incorporating a heat-exchanger and a cutting blade. The heat-exchanger pipes run through the interior space of the housing, while the scalpel has an electric heater to heat the blade (GB, A, 1,247,301).

The aforesaid scalpel operates on the principle of an alternative feeding of cold and heat, the former being generated by the heat-exchanger through which a refrigerant (i.e., a gas-liquid mixture) is free to circulate, while heat is generated by the electric heater. The cold thus generated is used for establishing hemostasis at the instant when biologic tissues are cut-through, with the result that the blade sticks to the tissues being dissected, which is counteracted by thawing the blade by heating.

Such a process features but a low dissection rate due to obligatory alternation of cold and heat and leads to a high degree of traumatization on account of tissue sticking to the blade. The scalpel has a low refrigerating capacity due to obligatory alternation of cooling and heating of the blade with the resultant inadequate hemostatic effect from the application of such a scalpel.

Besides, the scalpel is bulky and inconvenient in handling.

SUMMARY OF THE INVENTION

It is an object of the invention to provide a cryogenic scalpel whose construction would ensure a continuous feed of cold.

It is another object of the invention to provide high dissection rate of biological tissues.

It is one more object of the invention to reduce the degree of traumatic lesion inflicted upon biological tissues.

It is still one more object of the invention to cut down the operating time.

It is yet still one more object of the invention to reduce blood loss in the course of surgery.

The foregoing objects are accomplished by a cryogenic scalpel, wherein a hollow housing is connected to a working portion, which comprises a heat-exchanger communicating, through a piping, with a source of pressure, and a blade, according to the invention, incorporates a source of electromechanical oscillations enclosed in a hollow housing, and a unit for imparting electromechanical oscillations to the scalpel working portion, said unit being interconnected to the source of electromechanical oscillations.

Such a combination of the effect of ultralow temperatures with the effect of electromechanical oscillations provides for novel functional and physical properties of the present cryogenic scalpel, whereby the dissection rate of biologic tissue is increased and a high hemostatic effect is attained.

A vibrator may be used as a source of electromechanical oscillations and may be located on the piping communicating the heat-exchanger with the source of pressure and imparting reciprocating motion to the scalpel working portion.

It is expedient that the unit for imparting electromechanical oscillations be a rigid joint between the piping and the scalpel working portion and that said joint be located outside the hollow housing.

The piping may have a projection and a slot on its portion rigidly joined to the scalpel working portion, said slot being adapted to hold said working portion so as to establish a rigid joint therebetween.

It is expedient that the heat-exchanger be made integral with the body of the working portion and have an interior space and fins provided on the inner surface of the interior space, and that the fins be made integral with the body of the working portion.

It is preferred that the piping portion accommodated inside the hollow housing be made of steel.

In addition, it is preferred that the heat-exchanger be made of copper and that its outer surface be chromium-plated.

It is also expedient that the blade be attached to the heat-exchanger through its ends in such a manner that its cutting lip be isolated from the heat-exchanger so that only electromechanical oscillations could be imparted thereto.

BRIEF DESCRIPTION OF THE DRAWINGS

Further objects and advantages of the present invention will hereinafter be disclosed upon consideration of a detailed description of specific exemplary embodiments thereof with reference to the accompanying drawings wherein.

DETAILED DESCRIPTION OF THE INVENTION

Figure 1:
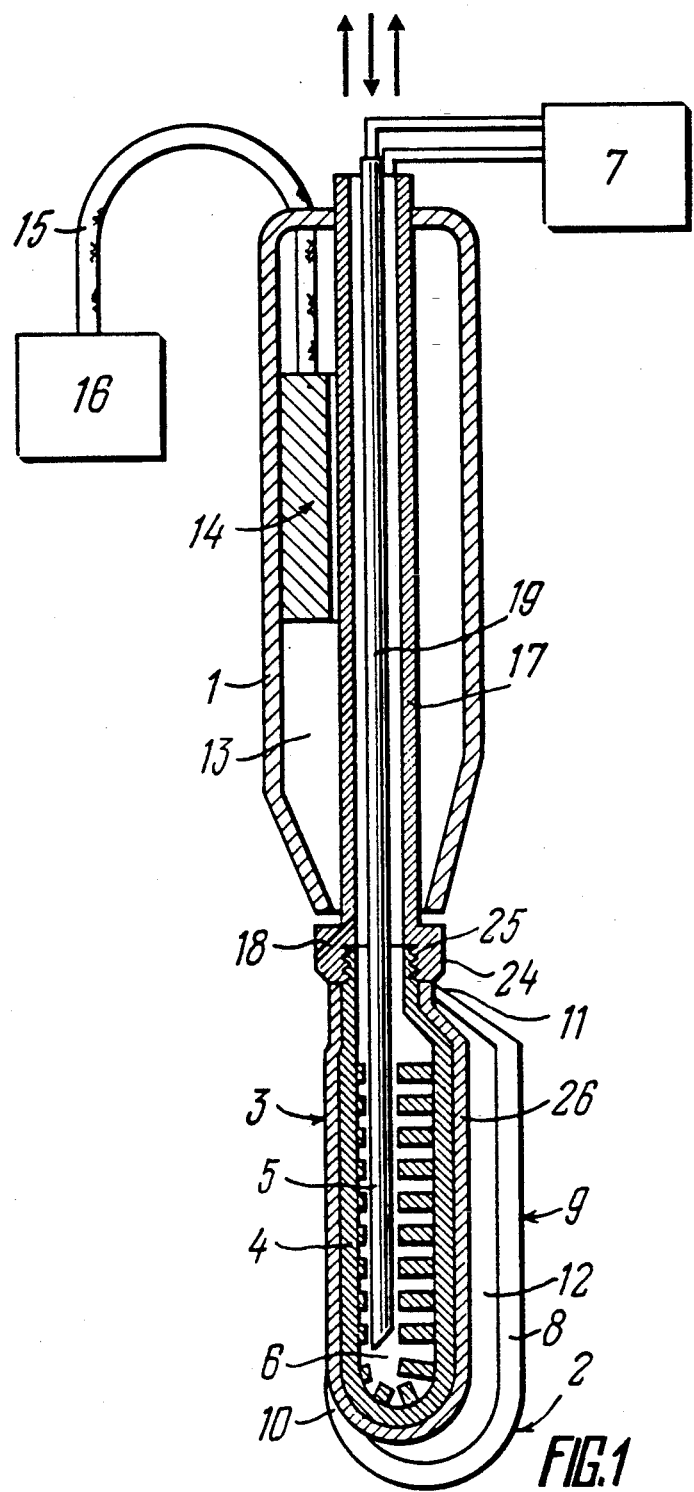
FIG. 1 is a longitudinal cross-sectional view of an embodiment of a cryogenic scalpel, according to the invention.

The cryogenic scalpel comprises a hollow housing 1 (FIG. 1) and a working portion 2 connected to the housing 1, which serves at the same time as a handle held by surgeon's hand.

The working portion 2 comprises a tubular heat-exchanger 3 composed of two coaxial pipes 4 and 5, the pipe 5 being adapted for feeding the refrigerant from a pressure source 7 into interior space 6 of the heat-exchanger 3, while the pipe 4 is for said refrigerant to be discharged from the heat-exchanger 3. Held in place to the heat-exchanger 3 is a blade 8 with a cutting lip 9. The blade 8 is attached on the outer surface of the heat-exchanger 3 with its two ends 10 and 11 in such a manner that a gap 12 is left between the blade 8 and the heat-exchanger 3.

An interior space 13 of the hollow housing 1 accommodates a source 14 of electromechanical oscillations interconnected, through a conductor 15, to a power source 16. The source 14 generates electromechanical oscillations, which are imparted, through a piping 17 communicating with the heat-exchanger 3 and situated in the interior space 13 of the housing 1, then through the heat-exchanger 3 and the unit 18 for imparting electromechanical oscillations, to the working portion 2.

The heat-exchanger 3 communicates with the pressure source 7 via the pipings 17 and 19, the refrigerant being admitted to the heat-exchanger 3 along the piping 19 and is discharged therefrom along the piping 17.

Used as the source 14 (FIG. 2) is a vibrator, comprising four electromagnets 20, 21, 22, 23 located on the piping 17 in the interior space 13, while the piping 17 itself serves a movable vibrator element and is made of steel.

The unit 18 is a rigid joint of the piping 17 and the pipe 4 of the heat-exchanger 3, said joint being located outside the housing 1. The pipe extension jutting out of the housing 1 has a projection 24 and a slot 25, wherein the pipe 4 is held, thus establishing said rigid joint for imparting electromechanical oscillations.

The working portion 2 shown in FIG. 1 has a body 26; it proves, however, to be more favorable, in view of higher refrigerating capacity of the heat-exchanger 3, that the body 26 of the scalpel working portion and the pipe 4 of the heat-exchanger 3 be made integral with each other as a single unit. Then the pipe 4 (FIG. 4) will serve at the same time the body of the working portion 2.

The blade 8 (FIG. 2) is a detachable one and is held to the heat-exchanger through, e.g., pins 27.

Figure 2:
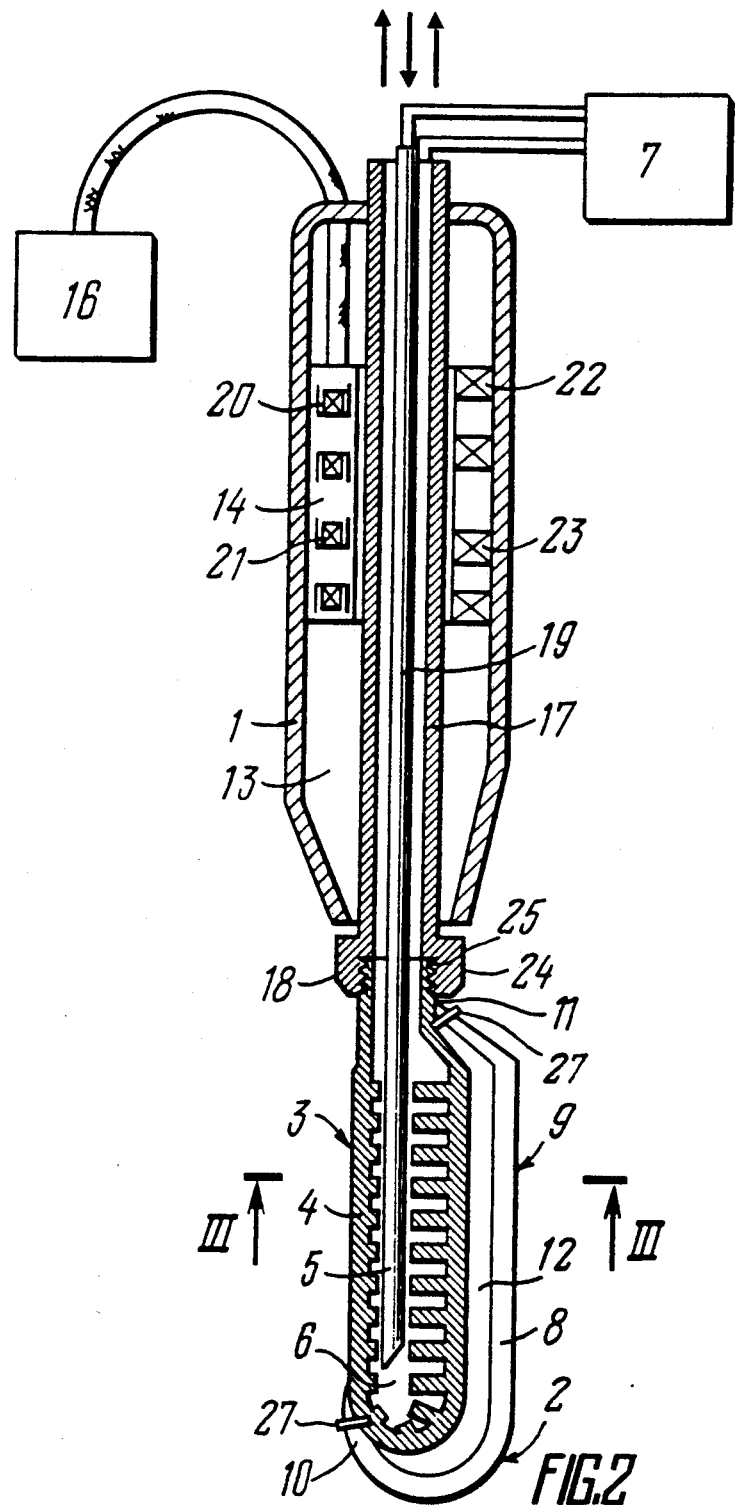
FIG. 2 is a longitudinal cross-sectional view of an alternative embodiment of a cryogenic scalpel, according to the invention.
Figure 3:
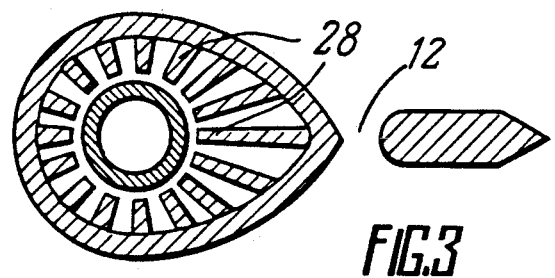
FIG. 3 is a section taken along the line III—III in FIG. 2.
Figure 4:
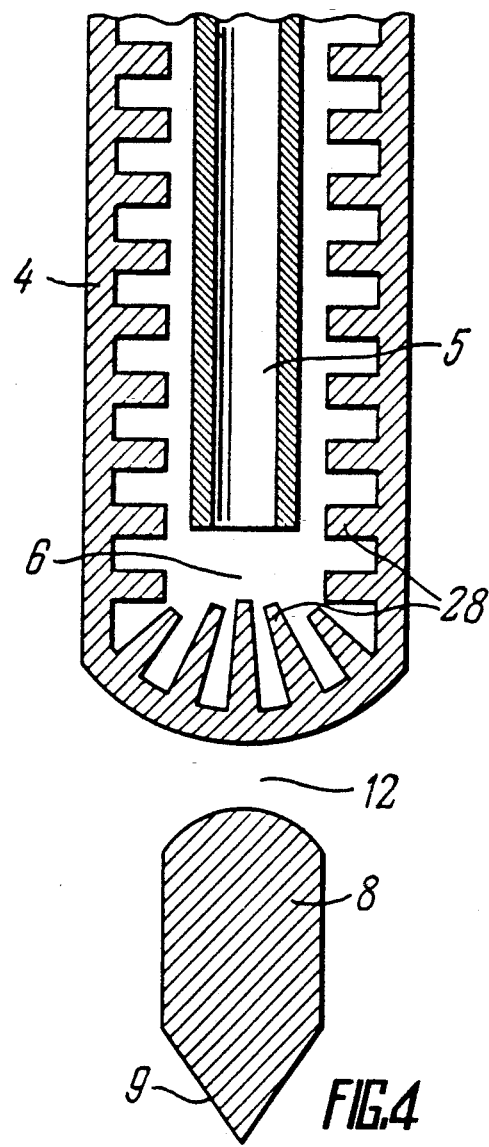
FIG. 4 is a scaled-up longitudinal sectional view of the scalpel working portion, according to the invention.

For the sake of higher refrigerating capacity a number of fins 28 (FIG. 3) are provided on the inner surface of the heat-exchanger 3 (FIG. 1) in its interior space 6, said fins 28 being either secured on the pipe 4 or are made integral with the pipe 4 as is the case in FIGS. 2 and 4.

The heat-exchanger 3 is made of a metal featuring high thermal conductivity, e.g., of copper, and its outer surface is chromium-plated.

Used as a refrigerant is a gas-liquid mixture, e.g., a mixture of liquid and gaseous nitrogen.

The cryogenic scalpel of the invention operates as follows.

The pipings 17, 18 are connected to the pressure source 7, while the vibrator 14 is connected to the power source 16. Then refrigerant is admitted to pass to the heat-exchanger 3 in order to cool the scalpel working portion 2. The spent refrigerant is discharged, as a gas-liquid mixture, from the interior space 6 along the piping 17. The scalpel working temperature setting time ranges from 3 to 5 minutes, when liquid nitrogen is used and an excess pressure from 220 to 380 mm Hg is applied. Once a working temperature of from 80 to 120 K. has been attained, the vibrator 14 is set in operation.

During surgery the scalpel exerts a complex effect, i.e., by cold and vibration. In this case the hemostatic effect is produced due to cooling of the tissue of the parenchymatous organs being cut, while vibration of the working portion 2, the blade 8 inclusive, prevents the tissues being cut from sticking to the blade 8 and to the heat-exchanger 3, thus reducing the degree of their traumatic lesion.

In the present scalpel the rate of heat inflow is much lower due to properly selected mode of vibrations, since heat transfer is low in case of electromechanical oscillations.

The temperature in the heat-exchanger is maintained almost constant throughout the surgical procedure. High refrigerating capacity of the heat-exchanger 3 is attained due to its being made integral with the fins 28 and manufactured from the same material.

Having selected an appropriate amplitude of oscillations, one should eliminate sticking of the biologic tissues being cut to the scalpel working portion 2 and maintain the tissue dissection rate approximately equal to the rate of cutting with a conventional scalpel.

Sticking is also eliminated by virtue of the air gap 12 left in between the blade 8 and the heat-exchanger 3. Provision of the detachable blade 8 and working portion 2 adds to the versatility of the present scalpel without affecting its refrigerating capacity.

A total of 12 experimental surgical procedures have been performed on test animals with the aid of the present cryogenic scalpel, said surgeries being made for resection of the liver, pancreas, spleen, and kidney.

In clinic there have been carried out two operations for resection of the liver (lobectomy and sectoral resection). Application of the cryogenic scalpel experimentally and clinically has demonstrated that it is suitable for dissecting the tissues of parenchymatous organs at a rate of a conventional surgical scalpel. Simultaneously there is attained arresting of the parenchymatous bleeding and bleeding from vessels up to 1.5 or 2 mm in caliber. Tissue injury involved is minimized, which reduces blood loss during surgery, provides for prompt surgical interference with minimiued tissue injury and cuts down postoperative wound healing period.

What is claimed is:

1. A cryogenic scalpel for conducting surgical operations on parenchymatous biological tissues, comprising:
a hollow housing having an interior space;
a working portion connected to said hollow housing and having a body extending in a lengthwise direction;
heat-exchanger means for establishing a zone for cooling biological tissues during surgery by supplying cooling fluid to said interior space;
a blade having two ends and a cutting lip, said ends of said blade being secured to said heat-exchanger means;
a coolant free to circulate through said heat-exchanger means;
a piping accommodated in said interior space of said hollow housing and communicating with said heat-exchanger means;
a source of electromechanical oscillations accommodated in said hollow housing to establish reciprocating motion to said working portion with a frequency of electromechanical oscillation with the result that heating of said blade is precluded and parenchymatous biological tissues are separated by simultaneously cooling in said cooling zone created by said heat-exchanger means; and means for imparting electromechanical oscillations to said working portion so as to transmit reciprocating motion to said blade; said means for imparting being connected between said source of electromagnetic oscillations and said blade.

2. A cryogenic scalpel as claimed in claim 1, wherein said source of electromechanical oscillations is a vibrator located on said piping.

3. A cryogenic scalpel as claimed in claim 1 or 2, wherein said unit for imparting electromechanical oscillations is a rigid joint between said piping and said working portion, said joint being situated outside said hollow housing.

4. A cryogenic scalpel as claimed in claim 3, wherein said piping extends beyond said hollow housing and has a projection and a slot, in which said working portion is held in place and which provides a rigid connection of said piping with said working portion.

5. A cryogenic scalpel as claimed in claim 1 or claim 2, wherein said heat-exchanger is made of copper.

6. A cryogenic scalpel as claimed in claim 5, wherein said heat-exchanger means has a chromium-plated outside surface.

7. A cryogenic scalpel for conducting surgical operations on parenchymatous biological tissues, comprising:
 a hollow housing having an interior space;
 a working portion connected to said hollow housing and having a body extending in a lengthwise direction;
 copper heat-exchanger means for establishing a zone for cooling biological tissues during surgery;
 a blade having two ends and a cutting lip, said blade secured to said heat-exchanger means through said ends in such a manner that said cutting lip is separated from said heat-exchanger means for imparting said cutting lip with electromechanical oscillations;
 a cooling agent free to circulate in said heat-exchanger means;
 a piping accommodated in said interior space of said hollow housing and connected to said heat-exchanger means;
 a source of electromechanical oscillations constructed as a vibrator and accommodated in said hollow housing on said piping to establish reciprocating motion of said working portion;
 means for imparting electromechanical oscillations to said working portion so as to transmit reciprocating motion to said blade, only in the lengthwise direction of said working portion, said means being a rigid joint between said piping and said working portion, said joint being situated outside said hollow housing so as to connect said source of electromagnetic oscillations to said blade; and
 said heat-exchanger means being a single unit with said body of said working portion and having an interior space and a plurality of fins on the interior surface of said space of said heat-exchanger means in which said plurality of fins are made monolithic with said body of said work portion.

8. A cryogenic scalpel as claimed in claim 7, wherein said piping extends beyond said hollow housing and has a projection and a slot, in which said working portion is securely fastened to provide a rigid joint of said piping and said working portion.

9. A cryogenic scalpel as claimed in claim 7 or claim 8, wherein said heat-exchanger means has a chromium-plated outside surface.

10. A cryogenic scalpel as claimed in claim 1 or claim 2, in which said heat-exchanger means is made integral with said body of said working portion and has a space and a plurality of fins on the interior surface of said space of said heat-exchanger means in which said plurality of fins are made monolithic with said body of said working portion.

* * * * *